(12) United States Patent
Rogerson et al.

(10) Patent No.: US 6,416,739 B1
(45) Date of Patent: Jul. 9, 2002

(54) MICROPARTICLES AND THEIR THERAPEUTIC OR DIAGNOSTIC USE

(75) Inventors: Cheryl Vanessa Rogerson; Nicholas David Osborne, both of Nottingham (GB)

(73) Assignee: Quadrant Healthcare (UK) Limited, Ruddington (GB)

( * ) Notice: Subject to any disclaimer, the term of this patent is extended or adjusted under 35 U.S.C. 154(b) by 94 days.

(21) Appl. No.: 09/582,145

(22) PCT Filed: Dec. 21, 1998

(86) PCT No.: PCT/GB98/03853

§ 371 (c)(1),
(2), (4) Date: Jul. 20, 2000

(87) PCT Pub. No.: WO99/32083

PCT Pub. Date: Jul. 1, 1999

(30) Foreign Application Priority Data

Dec. 22, 1997 (GB) .............................................. 9727102

(51) Int. Cl.⁷ ........................... A61B 8/00; B32B 15/02; B32B 11/00
(52) U.S. Cl. ................ 424/9.5; 428/402.2; 428/402.21; 428/402.24; 424/9.51; 424/46; 424/489; 424/490; 424/491; 424/493; 424/499; 424/501; 521/60; 521/134

(58) Field of Search ........................... 428/402.2, 402.21, 428/402.24; 424/9.5, 9.51, 489, 490, 491, 493, 499, 501, 46; 521/60, 134

(56) References Cited

U.S. PATENT DOCUMENTS

| | | | | |
|---|---|---|---|---|
| 3,957,964 A | * | 5/1976 | Grim, III | 424/10 |
| 4,180,593 A | * | 12/1979 | Cohan | 426/72 |
| 4,971,787 A | * | 11/1990 | Cherukuri et al. | 414/48 |
| 5,202,159 A | * | 4/1993 | Chen et al. | 427/213.31 |

FOREIGN PATENT DOCUMENTS

| | | | |
|---|---|---|---|
| WO | WO92/18164 | * | 10/1992 |
| WO | WO96/15814 | * | 5/1996 |
| WO | WO98/31346 | * | 9/1998 |

* cited by examiner

Primary Examiner—Samuel A. Acquah

(57) ABSTRACT

Microcapsules having a wall thickness of no more than 500 nm, and a bulk density of no more than 0.2 g.cm⁻³, are suitable for therapeutic or diagnostic use. They are aerodynamically light, and can be used for delivery to the lung, or diagnosis by ultrasound.

41 Claims, No Drawings

MICROPARTICLES AND THEIR THERAPEUTIC OR DIAGNOSTIC USE

FIELD OF THE INVENTION

This invention relates to microparticles and their therapeutic or diagnostic use. More particularly, the invention relates to the delivery of an active agent to the lungs, by inhalation, and to diagnostic imaging using ultrasound.

BACKGROUND OF THE INVENTION

Edwards et al, Science 276: 1868–71 (1997), reports the production of particles of small mass density and large size, for use in pulmonary drug delivery. The objective was to provide an insoluble matrix which could act as a reservoir for sustained drug release, analogous to a sustained release tablet. Porous and non-porous particles were prepared, the porous particles being preferred for their "high efficiency". The "particle mass density" values for these particles were about 0.1 g.cm$^{-3}$ and 0.8 g.cm$^{-3}$, respectively. The porous particles apparently comprised a solid matrix including pores, the matrix being essentially a carrier for a therapeutic agent (the given examples being testosterone and insulin) held within the matrix.

Note 14 of Edwards et al states that the density is determined by non-mercury porosimetry or tap density measurements. The latter at least would not give a true particle density. Reference 15 (French et al, J. Aerosol Sci. 27:769 (1996)) clearly shows bulk densities. Note 14 refers to Vidgren et al, Int. J. Pharm. 35:139 (1987), which uses an "effective density". Hence, little can be concluded as to the meaning of "particle mass density".

WO 98/31346 apparently relates to products similar to those disclosed by Edwards et al. The particles are aerodynamically light, and generally porous.

A difficulty with many sustained release inhalation therapies is that solid (or more dense) particles will be subject to clearance mechanisms and therefore unable to act as a reservoir. Any such particles landing in the trachea or bronchi will be rapidly removed by mucociliary clearance mechanisms. Similarly, particles reaching the non-ciliated regions of the deep lung are rapidly cleared by macrophage activity. The material reported by Edwards et al is intended to avoid both these problems, by providing a particle of relatively large geometric diameter (>5 μm) which will avoid phagocytosis by macrophages, but which is aerodynamically small (i.e. a low density with respect to geometric diameter), and which will reach the non-ciliated region of the deep lung. Sustained release is then achieved by use of an insoluble matrix of material.

The particles disclosed by Edwards et al. were prepared by double- and single-emulsion solvent evaporation techniques. It is also stated that porous particles comprising therapeutics and pharmaceutical excipients can easily be formed by spray-drying, and refers in this context to an article by Sacchetti and van Oort in "Inhalation Aerosols" (May 1996) A J Hickey ed., Dekker N.Y. pub., pages 337–384. No specific indication is given as to how particles of low density might be obtained by spray-drying. For inhalation therapy, a dry powder must be dispersed into an airstream as discrete particles, to ensure controlled reproducible administration of a standard dose. To achieve this, the powder is usually loaded onto a carrier such as lactose, through blending. The objective is to produce a blend in which the drug powder is distributed as discrete particles evenly over the carrier. If this is not achieved, and the particles are agglomerates, there is an apparent increase in aerodynamic size and a reduction in dosing efficiency.

While compounds that can be administered without carrier are known, e.g. sodium cromoglycate and terbutaline, these are usually either extremely safe or relatively inactive, allowing therapeutic effects to be achieved as a result of the inefficient administration of enormous quantities of material. Moreover, the use of carriers can cause additional drug formulation difficulties. For example, lactose, the most commonly used material for this purpose, is a reducing sugar and can react chemically with some drug substances, such as proteins and peptides.

The mechanical manipulation of lactose, such as blending and sieving, also results in "high energy spots" on the surface of the carrier. This results in a reduction of inhalation efficiency, because of the additional energy required to disperse the drug material.

The use of spray-drying in pharmaceutical processing is not new. However, it is usually used to bind particles together, for the purposes of obtaining powders with good flow properties.

U.S. Pat. No. 5,202,159 describes spray-drying a slurry of diclofenac, excipients, methacrylic acid-ethyl acrylate copolymers and polyethylene glycol, and formulating the product into tablets. U.S. Pat. No. 4,971,787 discloses spray-drying a medicament with sugar, and formulating the product with a specific gum base, to give a chewing gum composition.

U.S. Pat. No. 4,180,593 discloses producing free-flowing blown bead food products, by spray-drying the foodstuff with a blowing agent, and then quenching, in order to control the bulk density. The reported bulk density in the only Example is about 0.1 g.cm$^{-3}$ (6 lb/ft$^3$).

SUMMARY OF THE INVENTION

By contrast to the prior use of spray-drying, for bonding particles together in a medicament, the present invention uses spray-drying for the production of large, light particles. More particularly, it has now been found that microcapsules having properties that are particularly suitable for use in ultrasound diagnostic procedures, i.e. non-porous, and for the delivery of a therapeutic agent by inhalation, can be prepared by the simple expedient of including a blowing agent in the formulation to be spray-dried. As a result, microcapsules having a bulk density of no more than 0.2 g.cm$^{-3}$ can be obtained.

Microcapsules of the invention are very suitable for formulation in an inhaler. If they comprise a therapeutic agent, they provide rapid release and subsequent uptake of drug in the lung, and avoid drug encapsulation, quite by contrast to any sustained release formulation. Further, products of this invention do not require a carrier, for effective administration to the lung. An inhaler including microcapsules of the invention may therefore contain the microcapsules as the sole or predominant component of the inhalable formulation.

Thus, the present invention allows the controlled, reproducible administration of small quantities of potent and/or expensive medicines without the need for carrier material. Problems associated with the use of lactose can be avoided.

Moreover, if the microcapsules contain only wall-forming material, and no therapeutic agent is included as such, they are particularly suitable for use in ultrasonic imaging. The relatively thin walls of the microcapsules apparently provides improved echogenicity.

DESCRIPTION OF THE INVENTION

Procedures for preparing microparticles by spray-drying, suitable wall-forming materials (such as albumin), and processes for stabilising the microparticles, e.g. by heat or chemically, are fully described in, inter alia, WO 92/18164 and WO 96/15814 (describing the currently preferred process), the contents of which are incorporated herein by reference. According to the present invention, these procedures are modified by the inclusion of a blowing agent, in the feedstock for spray-drying.

The blowing agent is a volatile substance which releases a gas or gases during the spray-drying process. Blowing agents are used in the present invention, to produce hollow microcapsules. Suitable blowing agents include ammonium acetate, ammonium hydroxide, ammonium carbonate, ammonium bicarbonate, acetic acid, formic acid and hydrochloric acid. The pH at which these blowing agents are used may vary; this implies that compounds with pH-dependent solubilities can be spray-dried with the addition of a suitable blowing agent.

By way of example, the blowing agent used in the production of albumin microcapsules is ammonium carbonate which releases ammonia, carbon dioxide and water vapour. During spray-drying, these three gases expand in the atomised droplets, causing the droplet to increase in size, to produce larger, thinner-walled microcapsules.

Products of the invention may have various characteristics, depending on the conditions of their preparation. For example, their median size is 1 to 20 $\mu$m, and their wall thickness is no more than 500 nm, e.g. 10 to 250 nm, more preferably 100 to 150 nm. Their bulk density may be 0.01 to 0.15 g.cm$^{-3}$, more preferably 0.04 to 0.1 g.cm$^{-3}$.

The microcapsules of the invention comprise a wall-forming material and, if desired, a therapeutic agent (which may be the same). If the wall-forming material and the therapeutic agent are different, the microcapsules may be formed by co-spray-drying.

As indicated above, the microcapsules may comprise albumin, and preferably human serum albumin. Albumin may be used as a therapeutic agent per se, or as a wall-forming material in combination with a therapeutic agent. Other active agents for use in the invention will be chosen having regard to the desired effect. Examples of active agents that may be used include cotranscytosis factors, fibrinogen, thrombin, insulin, growth hormone, calcitonin, $\alpha$-antitrypsin, FSH, $\alpha$-interferon, $\beta$-interferon, heparin, Factor VIII, Factor IX, interleukins and blood coagulation factors. Other wall-forming materials that may be used are described in WO 92/18164.

For the preferred route of administration, the soluble microcapsules obtained by spray-drying are used. As indicated above, stabilisation may be used, if another route of administration is required and/or for diagnostic purposes. The amount of microcapsules to be administered can readily be determined by the skilled man.

The following Examples illustrate the invention.

EXAMPLE 1

212 ml diafiltered 10% w/w HSA solution containing 60 g ammonium carbonate was spray-dried on a standard Mobile Minor spray-dryer. The conditions were as follows:

| | |
|---|---|
| Inlet temperature – | 220° C. |
| Atomisation pressure – | 2.0 barg |
| Feed rate – | 21.4 g/min |
| Atomisation type – | 2-fluid nozzle |
| Liquid insert – | 0.5 mm |

The non-fixed microcapsules obtained by spray-drying, which are soluble, behaved as a powder, demonstrating liquid fluidised properties. They are suitable for use as such, in an inhaler.

For testing purposes, 4 g microcapsules obtained by spray-drying were heat-stabilised for 55 minutes at 176° C. in a hot air oven. After heat stabilisation, the microcapsules retained their fluidized properties.

A 50 mg aliquot of heat-stabilised microcapsules was dispersed in de-ionised water (sonication in ethanol was not necessary). The suspension was then microscopically examined and sized using a Coulter Counter fitted with a 50 $\mu$m aperture tube.

Microscopic examination showed the presence of 2 distinct populations of microcapsules. The first population consisted of hollow, air-containing microcapsules approx. 5 $\mu$m in size, and the second population consisted of larger, blown microcapsules containing the suspension fluid. Microcapsules of both populations may be suitable for use in accordance with the invention, independently or in combination.

The microcapsules had very thin walls. They were self-fluidising and had a density of approximately 0.07 g/cm$^3$. They were therefore suitable for testing as products for delivery by the pulmonary route. The median size by volume distribution of these microcapsules was shown to be 10.7 $\mu$m by Coulter Counter sizing.

Using a multi-stage liquid impinger (MLSI) and a Dinkihaler, the aerodynamic diameter of the microcapsules was determined.

Three gelatin capsules were each filled with 10 mg of the microcapsules. Each stage of the MLSI was filled with 20 ml purified water, and the air flow set to 60 l/minute.

A single gelatin capsule was pierced at both ends and placed in the Dinkihaler. The air flow was turned on for 30 seconds and then switched off.

The device and throat were each washed with 20 ml purified water. Each stage was washed in a total of 25 ml purified water and the filter was washed in 10 ml purified water. They were then assayed for protein by standard methods.

The MLSI was washed thoroughly and prepared for a second run as described above. 3 runs were carried out. Results are shown in the following Table.

| | Percentage Accumulation | | |
|---|---|---|---|
| Stage | Run 1 | Run 2 | Run 3 |
| Device | 17.02 | 8.85 | 14.27 |
| Throat | 22.62 | 11.57 | 18.08 |
| 1 (>13.4 $\mu$m) | 4.78 | 2.66 | 5.31 |
| 2 (13.4-6.8 $\mu$m) | 14.58 | 18.30 | 12.99 |
| 3 (6.8-3.1 $\mu$m) | 25.92 | 32.63 | 23.56 |
| 4 (3.1-1.7 $\mu$m) | 7.96 | 15.59 | 11.09 |
| Filter (<1.7 $\mu$m) | 1.38 | 4.64 | 7.58 |
| Total Recovery (%) | 94.30 | 94.23 | 92.87 |

The respirable fractions (defined as particles below 6.8 $\mu$m) for runs 1–3 were 33%, 53% and 42%, respectively. The results are also representative of the non-stabilised microcapsules, and suggest that this type of microcapsule is suitable for pulmonary delivery.

EXAMPLE 2

100 ml of diafiltered 20% w/w HSA solution containing 10 g ammonium carbonate was spray-dried on a Niro Mobile Minor spray-dryer. The following conditions were used:

| | |
|---|---|
| Inlet temperature – | 220° C. |
| Atomisation pressure – | 7.5 barg |
| Feed rate – | 3.96 g/min |
| Atomisation type – | 2-fluid nozzle |
| Liquid insert – | 0.5 mm |

5 g of the spray-dried microcapsules thus obtained were heat-stabilised for 55 minutes at 177° C. in a hot air oven. The stabilised microcapsules were then deagglomerated with an equal mass of glucose using a Fritsch centrifugal pin mill.

The microcapsules were sized using a Coulter Counter fitted with a 100 μm orifice tube which found that the volume median diameter of the microcapsules was 10.1 μm. The echogenic properties were characterised as described in Example 5 of WO 96/15814. The known microcapsules were found to have echogenicities of around 26 VDU's; for the microcapsules of this Example, containing a blowing agent, the corresponding value was 69 VDU's.

What is claimed is:

1. A composition comprising microcapsules, wherein said microcapsules have a wall thickness of no more than 500 nm, and a bulk density of no more than 0.2 g.cm$^{-3}$.

2. The composition, according to claim 1, wherein the median size of said microcapsules is from 1 to 20 μm.

3. The composition, according to claim 1, wherein the wall thickness of said microcapsules is from 10 to 250 nm.

4. The composition, according to claim 3, wherein the wall thickness of said microcapsules is from 100 to 150 nm.

5. The composition, according to claim 1, wherein the bulk density of said microcapsules is from 0.01 to 0.15 g.cm$^{-3}$.

6. The composition, according to claim 5, wherein the bulk density of said microcapsules is from 0.04 to 0.1 g.cm$^{-3}$.

7. The composition, according to claim 1, wherein the walls of said microcapsules are comprised at least predominantly of albumin.

8. The composition, according to claim 1, obtainable by spray-drying a wall-forming material, in combination with a blowing agent.

9. The composition, according to claim 1, wherein said microcapsules comprise a therapeutic agent.

10. The composition, according to claim 9, wherein said microcapsules comprise a cotranscytosis factor.

11. The composition, according to claim 9, wherein said microcapsules comprise fibrinogen or thrombin.

12. The composition, according to claim 9, wherein said microcapsules comprise an active agent selected from the group consisting of insulin, growth hormone, calcitonin, α-antitrypsin, FSH, α-interferon, β-interferon, heparin, Factor VIII, Factor IX, interleukins and blood coagulation factors.

13. The composition, according to claim 9, which is soluble.

14. An inhaler comprising an inhalable formulation of microcapsules wherein said microcapsules have a wall thickness of no more than 500 nm, and a bulk density of no more than 0.2 g.cm$^{-2}$ and wherein said microcapsules comprise a therapeutic agent.

15. The inhaler according to claim 14, wherein the formulation comprises the microcapsules as the sole or the predominant component thereof.

16. The composition, according to claim 1, which is insoluble.

17. A method for pulmonary administration of a therapeutic agent wherein said method comprises the administration to the lungs of a composition which comprises microcapsules having a wall thickness of no more than 500 nm and a bulk density of no more than 0.2 g.cm$^{-3}$, wherein said microcapsules further comprise a therapeutic agent.

18. The method, according to claim 17, wherein the median size of said microcapsules is from 1 to 20 μm.

19. The method, according to claim 17, wherein the wall thickness of said microcapsules is from 10 to 250 nm.

20. The method, according to claim 17, wherein the wall thickness of said microcapsules is from 100 to 150 nm.

21. The method, according to claim 17, wherein the bulk density of said microcapsules is from 0.01 to 0.15 g.m$^{-3}$.

22. The method, according to claim 17, wherein the bulk density of said microcapsules is from 0.04 to 0.1 g.m$^{-3}$.

23. The method, according to claim 17, wherein the walls of said microcapsules are comprised at least predominantly of albumin.

24. The method, according to claim 17, wherein said microcapsules are obtainable by spray-drying a wall-forming material, in combination with a blowing agent.

25. The method, according to claim 17, wherein said microcapsules comprise a therapeutic agent.

26. The method, according to claim 25, wherein said microcapsules comprise a cotranscytosis factor.

27. The method, according to claim 25, wherein said microcapsules comprise fibrinogen or thrombin.

28. The method, according to claim 25, wherein said microcapsules contain an active agent selected from the group consisting of insulin, growth hormone, calcitonin, α-antitrypsin, FSH, α-interferon, β-interferon, heparin, Factor VIII, Factor IX, interleukins, and blood coagulation factors.

29. The method, according to claim 17, wherein said composition is soluble.

30. The method, according to claim 17, wherein said composition is insoluble.

31. A method for diagnosis by ultrasound, wherein said method comprises administering to a patient in need of such diagnosis, a composition which comprises microcapsules having a wall thickness of no more than 500 nm and a bulk density of no more than 0.2 g.cm$^{-3}$.

32. The method, according to claim 31, wherein the median size of said microcapsules is from 1 to 20 μm.

33. The method, according to claim 31, wherein the wall thickness of said microcapsules is from 10 to 250 nm.

34. The method, according to claim 31, wherein the wall thickness of said microcapsules is from 100 to 150 nm.

35. The method, according to claim 31, wherein the bulk density of said microcapsules is from 0.01 to 0.15 g.m$^{-3}$.

36. The method, according to claim 31, wherein the bulk density of said microcapsules is from 0.04 to 0.1 g.m$^{-3}$.

37. The method, according to claim 31, wherein the walls of said microcapsules are comprised at least predominantly of albumin.

38. The method, according to claim 31, wherein said microcapsules are obtainable by spray-drying a wall-forming material, in combination with a blowing agent.

39. A method for preparing microparticles, wherein said method comprises spray-drying wall-forming materials and wherein said method further comprises inclusion of a blowing agent in the feedstock for spray-drying.

40. The method, according to claim 39, wherein said blowing agent is selected from the group consisting of ammonium acetate, ammonium hydroxide, ammonium carbonate, ammonium bicarbonate, acetic acid, formic acid, and hydrochloric acid.

41. The method, according to claim 39, wherein said wall-forming material is albumin.

* * * * *